United States Patent
Workman et al.

(10) Patent No.: US 12,334,202 B2
(45) Date of Patent: Jun. 17, 2025

(54) SMART BARCODE ID FOR INTEROPERABLE PUMPS

(71) Applicant: CareFusion 303, Inc., San Diego, CA (US)

(72) Inventors: Michael K. Workman, Carlsbad, CA (US); Duc H. Nguyen, San Diego, CA (US)

(73) Assignee: CareFusion 303, Inc., San Diego, CA (US)

( * ) Notice: Subject to any disclaimer, the term of this patent is extended or adjusted under 35 U.S.C. 154(b) by 448 days.

(21) Appl. No.: 17/674,805

(22) Filed: Feb. 17, 2022

(65) Prior Publication Data
US 2022/0262476 A1 Aug. 18, 2022

Related U.S. Application Data

(60) Provisional application No. 63/151,004, filed on Feb. 18, 2021.

(51) Int. Cl.
*G16H 20/17* (2018.01)
*G06K 7/14* (2006.01)

(52) U.S. Cl.
CPC ........... *G16H 20/17* (2018.01); *G06K 7/1413* (2013.01)

(58) Field of Classification Search
CPC ........ G16H 10/60; G16H 20/17; G16H 40/20; G16H 40/40; G16H 40/60; G16H 40/63; G16H 40/67; A61M 5/142; A61M 5/172; A61M 5/50; G06K 7/1413; G06K 7/1417; G06K 19/06; A61B 5/117
(Continued)

(56) References Cited

U.S. PATENT DOCUMENTS

| 8,567,681 B2 | 10/2013 | Borges et al. |
| 10,218,411 B2 * | 2/2019 | Rovatti ..................... H04B 5/24 |

(Continued)

FOREIGN PATENT DOCUMENTS

CN 209662347 U 11/2019

OTHER PUBLICATIONS

International Search Report and Written Opinion for Application No. PCT/US2022/016843, dated May 11, 2022, 16 pages.

(Continued)

*Primary Examiner* — Alaaeldin M. Elshaer
(74) *Attorney, Agent, or Firm* — Morgan, Lewis & Bockius LLP

(57) ABSTRACT

An infusion system includes a network data transceiver and a processor configured to determine, at the infusion device, when the infusion device is in a prepared state. In response to determining that, and while, the infusion device is in the prepared state: the processor is configured to present, on a display of the infusion device, a unique identifier of the infusion device, wait for an indication that the unique identifier of the infusion device was scanned by a scanner to associate the infusion device with an infusion order. The processor is configured to receive configuration information associated with the infusion order, and automatically configure the infusion device to cause infusion of a medical fluid specified in the infusion order based on parameters of the infusion order provided by the received configuration information.

18 Claims, 6 Drawing Sheets

(58) Field of Classification Search
USPC .......................................................... 705/2, 3
See application file for complete search history.

(56) References Cited

U.S. PATENT DOCUMENTS

| | | | |
|---|---|---|---|
| 2004/0172301 A1* | 9/2004 | Mihai .................. | A61B 5/0002 705/2 |
| 2006/0200369 A1 | 9/2006 | Batch et al. | |
| 2009/0157432 A1* | 6/2009 | Palmroos .............. | A61M 5/142 700/83 |
| 2012/0241525 A1* | 9/2012 | Borges ............. | G06K 19/06112 235/494 |
| 2013/0098983 A1* | 4/2013 | Neff ................... | G06K 17/0025 235/375 |
| 2014/0067426 A1 | 3/2014 | Neff | |
| 2015/0371004 A1* | 12/2015 | Jones ..................... | G16H 70/40 705/2 |
| 2015/0379237 A1* | 12/2015 | Mills ..................... | A61M 5/142 705/2 |
| 2016/0058996 A1* | 3/2016 | Hoss ....................... | G16H 40/40 340/539.13 |
| 2016/0074573 A1 | 3/2016 | Kohlbrecher | |
| 2017/0061096 A1* | 3/2017 | Kelly ..................... | G16H 40/20 |
| 2019/0189272 A1* | 6/2019 | Kamen .................. | G16H 10/60 |
| 2021/0090730 A1* | 3/2021 | Patel .................... | G06F 3/04847 |
| 2022/0037012 A1* | 2/2022 | Fryman .................. | G16H 40/20 |

OTHER PUBLICATIONS

European Office Action for Application No. 22709462.0, dated Sep. 11, 2024, 9 pages.
Wikipedia, "Watchdog timer", Wikipedia the Free Encyclopedia, Watchdog timer page as edited by Lambtrom, Jan. 2021, XP93201960.

* cited by examiner

SMART BARCODE ID FOR INTEROPERABLE PUMPS

CROSS-REFERENCE TO RELATED APPLICATION(S)

This application claims priority to U.S. Provisional Patent Application No. 63/151,004, entitled "SMART BARCODE ID FOR INTEROPERABLE PUMPS," filed on Feb. 18, 2021, the entirety of which is incorporated by reference.

TECHNICAL FIELD

This application relates generally to safeguarding against failures to correctly initiate an infusion process using an unprepared infusion device.

BACKGROUND

Medical devices such as infusion devices are used to infuse medical fluids to patients. An infusion order may be sent from an electronic medical records storage and retrieval system to an infusion device used to infuse a medical fluid to a patient. An infusion pump should be in a prepared state to perform the steps needed to program the infusion and execute a programmed infusion. For example, without data connection between the infusion device and a data network system at the care facilities, the infusion device may not be able to receive the infusion order from the electronic medical records storage and retrieval system, and attempts to initiate an infusion process associated with the infusion order would fail. In a clinical setting, initiating an infusion process can be life-critical and consume precious resources (e.g., time, network bandwidth, device processor cycles, user interface space, etc.) which may be limited in certain operational environments.

SUMMARY

A caregiver may not be aware that an infusion device is unprepared to initiate an infusion. For example, the caregiver may not be aware that a data connection between the infusion device and a data network system at the care facilities has not yet been established, or has ceased. The caregiver who attempts to initiate the infusion process under such conditions may simply wait, in futile, for an infusion order to be sent from an electronic medical records storage and retrieval system to the infusion device, unaware that the infusion device is unable to receive such data. These types of failures may result in unproductive waiting times, user frustration, and may compromise patient safety if a time-sensitive infusion has to be timely administered to the patient. Indeed, the caregiver may not even be aware that remedial actions for reestablishing a data connection between the data network system and the infusion device need to be taken. In some instances, the attempt consumes resources to collect, prepare, and transmit the messages to initiate the infusion. These resources may be shared with other infusion devices or other processes of the infusion device. In clinical settings, the availability of resources can be critical to ensuring patient safety through responsive device adjustments as conditions change.

Accordingly, there is a need for systems, devices, and methods that help ensure the infusion device is prepared to initiate an infusion process. The preparedness may be evaluated using criterion characterizing the state of the infusion device. For example, criterion describing the state of data connectivity between the infusion device and the data network system may be used to determine whether the infusion device will enable initiation of an infusion process.

Part of the infusion preparation process may include associating an infusion order recorded at the electronic medical records storage and retrieval system to (1) a patient, (2) a bag of medication to be infused, and (3) the infusion device controlling an infusion pump. Associating the infusion order may include using a scanner to scan a unique identifier associated with the patient, for example, by scanning a unique identifier on a patient wristband. The unique identifier on the patient wristband may be a two-dimensional (2D) barcode. The bag of medication for the infusion may also have a unique identifier or barcode (e.g., 2D barcode) affixed to it.

When the unique identifier of the infusion device is permanently displayed (e.g., affixed as a physical barcode label to the infusion device, permanently displayed as a barcode on the infusion device), the caregiver may not notice indicator lights or icons signaling a lack of data connectivity between the infusion device and a data network system. Attempts to initial an infusion process may lead to wasted time in waiting for the electronic medical records storage and retrieval system to transmit infusion order information, which it is unable to do because of the lack of connectivity.

The disclosed devices, systems and methods dynamically control the infusion pump such as displaying the unique identifier of the infusion device for scanning by the scanner based on preconditions that are needed to process the unique identifier or information transmitted in response thereto. By not presenting the unique identifier on the display of the infusion device, the infusion pump prevents the infusion process from proceeding unless the connectivity issue, or other preconditions, is resolved.

The disclosed subject matter also relates to a method of ensuring certain preconditions are in place before a pump is configurable to submit an auto-programming request. If the conditions are met, the pump will display the indicia for initiating an auto-programming scan. If not all the preconditions are met, the pump will adjust or wait for the conditions to be satisfied before displaying the scan indicia. The method includes determining, at the infusion device, when the infusion device is in a prepared state to perform steps associated with programming an infusion and executing a programmed infusion; while, and in response to determining that, the infusion device is in the prepared state: presenting, on a display of the infusion device, a unique identifier of the infusion device; waiting for an indication that the unique identifier of the infusion device was scanned by a scanner to associate the infusion device with an infusion order; and receiving, at the infusion device, in response to receiving the indication, configuration information associated with the infusion order. The method includes automatically configuring the infusion device to cause infusion of a medical fluid specified in the infusion order based on parameters of the infusion order provided by the received configuration information; and in response to determining that the infusion device is not in the prepared state, removing the unique identifier from the display of the infusion device. The method may be implemented using a system that includes one or more processors and a memory including instructions that, when executed by the one or more processors, cause the one or more processors to perform the steps of the method described herein.

Other aspects include corresponding apparatus, and computer program products for implementation of the corresponding system and its features.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

For a better understanding of the various described implementations, reference should be made to the Description below, in conjunction with the following drawings. Like reference numerals refer to corresponding parts throughout the figures and description.

DESCRIPTION

Reference will now be made to implementations, examples of which are illustrated in the accompanying drawings. In the following description, numerous specific details are set forth in order to provide an understanding of the various described implementations. However, it will be apparent to one of ordinary skill in the art that the various described implementations may be practiced without these specific details. In other instances, well-known methods, procedures, components, circuits, and networks have not been described in detail so as not to unnecessarily obscure aspects of the implementations.

Figure 1:
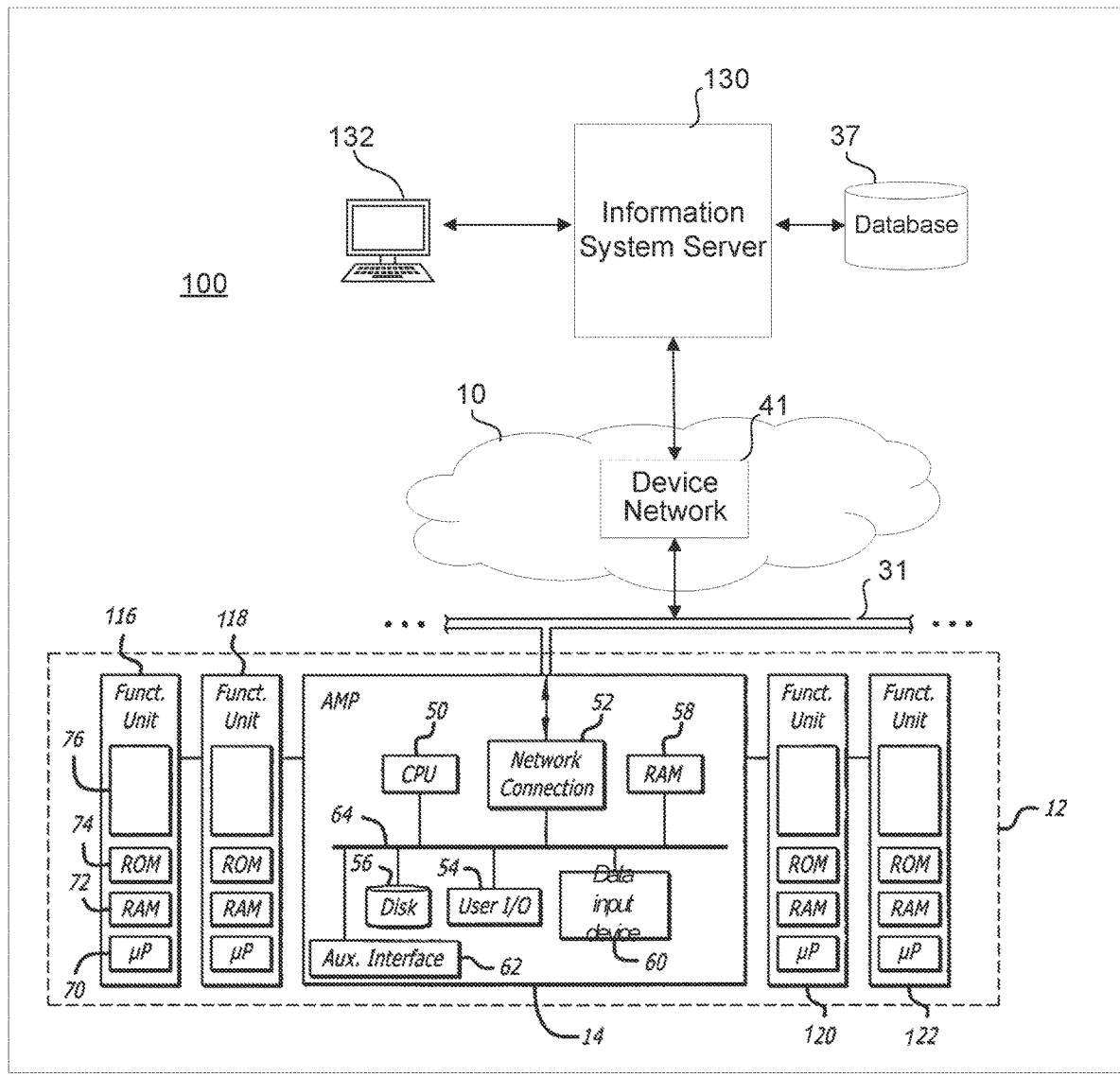
FIG. 1 depicts an example of an institutional patient care system of a healthcare organization, according to aspects of the subject technology.

FIG. 1 depicts an example of an institutional patient care system 100 of a healthcare organization, according to aspects of the subject technology. In FIG. 1, a patient care device (or "medical device" generally) 12 is connected to a hospital network 10. The term patient care device (or "PCD") may be used interchangeably with the term patient care unit (or "PCU"), either which may include various ancillary medical devices such as an infusion pump, a vital signs monitor, a medication dispensing device (e.g., cabinet, tote), a medication preparation device, an automated dispensing device, a module coupled with one of the aforementioned (e.g., a syringe pump module configured to attach to an infusion pump), or other similar devices. Each patient care device 12 is connected to an internal healthcare network 10 by a transmission channel 31. Transmission channel 31 is any wired or wireless transmission channel, for example an 802.11 wireless local area network (LAN). In some implementations, network 10 also includes computer systems located in various departments throughout a hospital. For example, network 10 of FIG. 1 optionally includes computer systems associated with an admissions department, a billing department, a biomedical engineering department, a clinical laboratory, a central supply department, one or more unit station computers and/or a medical decision support system. As described further below, network 10 may include discrete subnetworks. In the depicted example, network 10 includes a device network 41 by which patient care devices 12 (and other devices) communicate in accordance with normal operations.

Additionally, institutional patient care system 100 may incorporate a separate information system server 130, the function of which will be described in more detail below. Moreover, although the information system server 130 is shown as a separate server, the functions and programming of the information system server 130 may be incorporated into another computer, if such is desired by engineers designing the institution's information system. Institutional patient care system 100 may further include one or multiple device terminals 132 for connecting and communicating with information system server 130. Device terminals 132 may include personal computers, personal data assistances, mobile devices such as laptops, tablet computers, augmented reality devices, or smartphones, configured with software for communications with information system server 130 via network 10.

Patient care device 12 comprises a system for providing patient care, such as that described in Eggers et al., which is incorporated herein by reference for that purpose. Patient care device 12 may include or incorporate pumps, physiological monitors (e.g., heart rate, blood pressure, ECG, EEG, pulse oximeter, and other patient monitors), therapy devices, and other drug delivery devices may be utilized according to the teachings set forth herein. In the depicted example, patient care device 12 comprises a control module 14, also referred to as interface unit 14, connected to one or more functional modules 116, 118, 120, 122. Interface unit 14 includes a central processing unit (CPU) 50 connected to a memory, for example, random access memory (RAM) 58, and one or more interface devices such as user interface device 54, a coded data input device 60, a network connection 52, and an auxiliary interface 62 for communicating with additional modules or devices. Interface unit 14 also, although not necessarily, includes a main non-volatile storage unit 56, such as a hard disk drive or non-volatile flash memory, for storing software and data and one or more internal buses 64 for interconnecting the aforementioned elements.

In various implementations, user interface device 54 is a touch screen for displaying information to a user and allowing a user to input information by touching defined areas of the screen. Additionally or in the alternative, user interface device 54 could include any means for displaying and inputting information, such as a monitor, a printer, a keyboard, softkeys, a mouse, a track ball and/or a light pen. Data input device 60 may be an optical code reader capable of scanning and interpreting data printed or displayed in a graphic format such as a barcode or quick read code. Additionally or in the alternative, data input device 60 can be any device for entering coded data into a computer, such as a device(s) for reading a magnetic strips, radio-frequency identification (RFID) devices whereby digital data encoded in RFID tags or smart labels (defined below) are captured by the reader 60 via radio waves, PCMCIA smart cards, radio frequency cards, memory sticks, CDs, DVDs, or any other analog or digital storage media. Other examples of data input device 60 include a voice activation or recognition device or a portable personal data assistant (PDA). Depending upon the types of interface devices used, user interface device 54 and data input device 60 may be the same device. Although data input device 60 is shown in FIG. 1 to be disposed within interface unit 14, it is recognized that data input device 60 may be integral within pharmacy system 34 or located externally and communicating with pharmacy system 34 through an RS-232 serial interface or any other appropriate communication means. Auxiliary interface 62 may be an RS-232 communications interface, however any other means for communicating with a peripheral device such as a printer, patient monitor, infusion pump or other medical device may be used without departing from the subject technology. Additionally, data input device 60 may be a separate functional module, such as modules 116, 118, 120 and 122, and configured to communicate with controller 14, or any other system on the network, using suitable programming and communication protocols.

Network connection 52 may be a wired or wireless connection, such as by Ethernet, WiFi, BLUETOOTH, an integrated services digital network (ISDN) connection, a digital subscriber line (DSL) modem or a cable modem. Any direct or indirect network connection may be used, including, but not limited to a telephone modem, an MIB system, an RS232 interface, an auxiliary interface, an optical link, an infrared link, a radio frequency link, a microwave link or a WLANS connection or other wireless connection.

Functional modules 116, 118, 120, 122 are any devices for providing care to a patient or for monitoring patient condition. As shown in FIG. 1, at least one of functional modules 116, 118, 120, 122 may be an infusion pump module such as an intravenous infusion pump for delivering medication or other fluid to a patient. For the purposes of this discussion, functional module 116 is an infusion pump module. Each of functional modules 118, 120, 122 may be any patient treatment or monitoring device including, but not limited to, an infusion pump, a syringe pump, a PCA pump, an epidural pump, an enteral pump, a blood pressure monitor, a pulse oximeter, an EKG monitor, an EEG monitor, a heart rate monitor or an intracranial pressure monitor or the like. Functional module 118, 120 and/or 122 may be a printer, scanner, bar code reader or any other peripheral input, output or input/output device.

Each functional module 116, 118, 120, 122 communicates directly or indirectly with interface unit 14, with interface unit 14 providing overall monitoring and control of device 12. Functional modules 116, 118, 120, 122 may be connected physically and electronically in serial fashion to one or both ends of interface unit 14 as shown in FIG. 1, or as detailed in Eggers et al. However, it is recognized that there are other means for connecting functional modules with the interface unit that may be utilized without departing from the subject technology. It will also be appreciated that devices such as pumps or patient monitoring devices that provide sufficient programmability and connectivity may be capable of operating as stand-alone devices and may communicate directly with the network without connected through a separate interface unit or control unit 14. As described above, additional medical devices or peripheral devices may be connected to patient care device 12 through one or more auxiliary interfaces 62.

Each functional module 116, 118, 120, 122 may include module-specific components 76, a microprocessor 70, a volatile memory 72 and a nonvolatile memory 74 for storing information. It should be noted that while four functional modules are shown in FIG. 1, any number of devices may be connected directly or indirectly to controller unit 14. The number and type of functional modules described herein are intended to be illustrative, and in no way limit the scope of the subject technology. Module-specific components 76 include any components necessary for operation of a particular module, such as a pumping mechanism for infusion pump module 116.

While each functional module may be capable of a least some level of independent operation, interface unit 14 monitors and controls overall operation of device 12. For example, as will be described in more detail below, interface unit 14 provides programming instructions to the functional modules 116, 118, 120, 122 and monitors the status of each module. The programming instructions may be based a volume or flow rate detected using at least some of the features described.

Patient care device 12 is capable of operating in several different modes, or personalities, with each personality defined by a configuration database. The configuration database may be a database 56 internal to patient care device, or an external database 37. A particular configuration database is selected based, at least in part, by patient-specific information such as patient location, age, physical characteristics, or medical characteristics. Medical characteristics include, but are not limited to, patient diagnosis, treatment prescription, medical history, medical records, patient care provider identification, physiological characteristics or psychological characteristics. As used herein, patient-specific information also includes care provider information (e.g., physician identification) or a patient care device's 10 location in the hospital or hospital computer network. Patient care information may be entered through interface device 52, 54, 60 or 62, and may originate from anywhere in network 10, such as, for example, from a pharmacy server, admissions server, laboratory server, and the like.

Medical devices incorporating aspects of the subject technology may be equipped with a network interface module (NIM), allowing the medical device to participate as a node in a network. While for purposes of clarity the subject technology will be described as operating in an Ethernet network environment using the Internet Protocol (IP), it is understood that concepts of the subject technology are equally applicable in other network environments, such as wireless local area networks or wide area cellular networks, and such environments are intended to be within the scope of the subject technology.

Data to and from the various data sources can be converted into network-compatible data with existing technology, and movement of the information between the medical device and network can be accomplished by a variety of means. For example, patient care device 12 and network 10 may communicate via automated interaction, manual interaction or a combination of both automated and manual interaction. Automated interaction may be continuous or intermittent and may occur through direct network connection 54 (as shown in FIG. 1), or through RS232 links, MIB systems, RF links such as BLUETOOTH, IR links, WLANS, digital cable systems, telephone modems or other wired or wireless communication means. Manual interaction between patient care device 12 and network 10 involves physically transferring, intermittently or periodically, data between systems using, for example, user interface device 54, coded data input device 60, bar codes, computer disks, portable data assistants, memory cards, or any other media for storing data. The communication means in various aspects is bidirectional with access to data from as many points of the distributed data sources as possible. Decision-making can occur at a variety of places within network 10. For example, and not by way of limitation, decisions can be made in health information server (HIS) 30, decision support 48, remote data server 49, hospital department or unit stations 46, or within patient care device 12 itself.

Direct communications with medical devices operating on a network in accordance with the subject technology may be performed through information system server 30, also known as the remote data server (RDS). In accordance with aspects of the subject technology, network interface modules incorporated into medical devices such as, for example, infusion pumps or vital signs measurement devices, ignore all network traffic that does not originate from an authenticated RDS. The primary responsibilities of the RDS of the subject technology are to track the location and status of all networked medical devices that have NIMs, and maintain open communication.

Figures 2A, 2B:
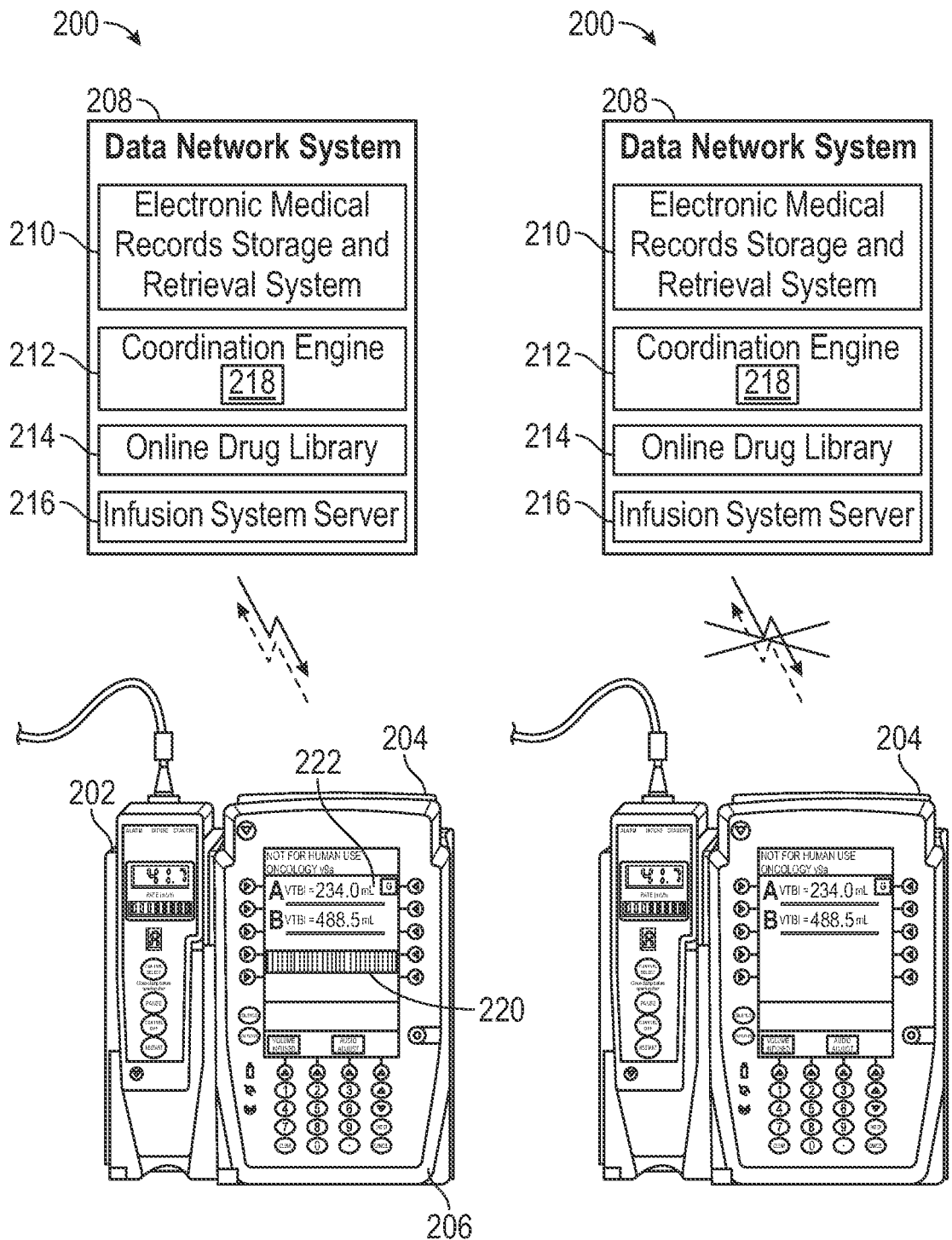
FIG. 2A depicts an example of a system for ensuring the infusion device is in a prepared state to perform the steps needed to program the infusion and execute a programmed infusion, according to aspects of the subject technology.
FIG. 2B depicts the system shown in FIG. 2A, when the infusion device is not ready for auto-programming because there is no data connection between the infusion device and the data network system, according to aspects of the subject technology.

FIG. 2A depicts an example of a system for ensuring a data connection between an infusion device and a data network system, according to aspects of the subject technology. The system 200 includes an infusion pump 202 controlled by an infusion device 204. The infusion device 204 may control additional infusion pumps in addition to the infusion pump 202. In some implementations, the infusion device 204 includes a communication module 206 (e.g., a wireless communication module, a wired communication module).

The system 200 allows for interoperability by establishing data connections between a data network system 208 and the infusion device 204. The data network system 208 may include an electronic medical records storage and retrieval system 210, a coordination engine 212, an online drug library 214, and an infusion system server 216. In some implementations, the coordination engine 212 includes an infusion adaptor 218. The infusion adaptor 218 provides a template to the coordination engine 212 to allow different preconfigured internal messaging protocols to be built for different infusion-specific applications of the infusion device 204.

The electronic medical records storage and retrieval system 210 (hereinafter "EMR system 210") stores, for a particular patient, infusion orders and other medications prescribed by a doctor to that particular patient. In addition, the EMR system 210 may also create auto-programming request (APR) messages that are delivered to the infusion device 204 to program the infusion pump 202 for a particular infusion order.

In some implementations, the APR messages that are sent to the infusion device are routed through the coordination engine 212 and the infusion system server 216. In some implementations, the coordination engine 212 interacts with the infusion device 204 via the infusion adaptor 218. The infusion adaptor 218 is an application that interfaces between the infusion device 204 and the coordination engine 212. The coordination engine 212 may perform various functions, including checking that the order information in the APR messages sent from the EMR system 210 to the infusion device 204 is complete and no required fields are missing or contain invalid data values.

In some implementations, an infusion process begins when a medical personnel (e.g., a doctor) prescribes an infusion order for a medication to a patient. The same or a different medical personnel (e.g., a pharmacist, a nurse) may then verify the infusion order and the order is added to the patient's medical record in the EMR system 210.

A caregiver (e.g., a nurse) at a site where the patient is to receive the infusion can access the medical record of the patient from the caregiver's workstation, or the infusion device, and may be notified of when a pending infusion order is to be provided to the patient. The caregiver may then retrieve a bag of medication specified in the infusion order from a pharmacy or medication storage and prepares for the infusion.

In some implementations, the EMR system 210 has an associated software program that is installed or deployed on the caregiver's workstation, or within the infusion device 204. The software receives and processes communication data from a scanner communicatively coupled to the workstation or infusion device 204 (e.g., via Bluetooth, Bluetooth Low Energy, Wi-Fi, near-field communication (NFC), Zig-Bee, etc.). The scanner may associate the infusion order (received from the EMR system 210) to (1) a particular patient, (2) the bag of medication for the infusion, and (3) the infusion pump 202 (or module).

Using the scanner, a patient may be identified to the system by way of scanning a patient wristband that contains a barcode or other unique identifier. The bag of medication for the infusion may also have a unique identifier or barcode affixed to it, and which also may be scanned by the scanner. For example, the scanner may be controlled by software operating on the infusion device 204, or on the caregiver's workstation to expect, in a first scan, the unique identifier on the patient's wristband. When the scanner transmits the information to the infusion device or workstation, the data system 208 may ascertain the identity of the patient, and may recognize that a pending infusion order is entered in the system for the patient. The scanner may then be controlled to collect, via a second scan, the unique identifier affixed to the bag of medication. After the scanner transmits the information about the bag of medication to the data system 208, the scanner may then be controlled to collect, via a third scan, a unique identifier associated with the infusion device 204.

The unique identifier may be presented by the infusion device 204 such as via a display included in the infusion device 204. The unique identifier may be associated with the infusion device 204 or a module attached to the infusion device. Presentation of the unique identifier may be conditional based on the readiness of the infusion device 204 (or module attached thereto) to perform an infusion. The readiness may be assessed by the infusion device 204 using one or more criteria. The criteria may be stored in a memory accessible by the infusion device 204. The criteria may include specific operational parameter ranges or values such as power level, wireless signal strength, alarm or alert state, or the like. The infusion device 204 may then detect or measure the applicable operational parameter and compare the measured value with the criteria. The infusion device 204 may determine whether it is ready for auto programming based on a correspondence between the measured value and the criteria.

For example, in some implementations, a data connection between the communication module 206 and the data network system 208 is first established in order for the EMR system 210 to send the correct order parameters (e.g., fluid flow rate, infusion time, infusion volume, etc.) to the infusion device 204 (or the infusion pump 202) to begin the infusion process for the correct patient. For systems in which the unique identifier of the infusion device is permanently displayed (e.g., affixed as a physical barcode label to a surface of the infusion device, permanently displayed as a barcode on a portion of the infusion device, permanently displayed as a barcode on a portion of a display of the infusion device), indicator lights or icons signaling a lack of data connectivity between the infusion device and a data network system may not be readily recognized. To avoid unnecessary delays or resource utilization by the infusion device attempting to perform an operation during an interruption in data connection, and to ensure that the communication module 206 maintains a data connection to the data network system 208, a unique identifier 220 associated with the infusion device 204 may not be shown on a display 222 of the infusion device 204 unless the data connection is established (i.e., the connectivity criteria for auto programming is satisfied).

According to various implementations, APR messages from the EMR system 210 to the infusion device 204 are directed to a particular infusion pump 202 of the infusion device 204. The infusion device may enable a start button to be triggered to begin the infusion on that particular infusion pump 202. For systems in which the unique identifier of the infusion pump 202 is permanently displayed (e.g., affixed as a physical barcode label to a surface of the infusion pump, permanently displayed as a barcode on a portion of the infusion device, permanently displayed as a barcode on a portion of a display of the infusion device associated with the infusion pump), indicator lights or icons signaling a lack of data connectivity between the particular infusion pump and the data network system may not be readily recognized. To provide a more intuitive and quicker visual feedback and conserve pump resources needed to process auto-programming requests or orders, the unique identifier 220 for a particular infusion pump 202 is only shown when the infusion pump 202 is ready to receive an infusion order and begin an infusion process. For example, an operational status associated with the infusion device 204 and/or the infusion pump 202 indicates whether at least one infusion pump 202 is ready to receive a new or incoming infusion order. The operation status of the infusion pump 202 or infusion device 204 may be indicated as unavailable when the infusion device 204 is undergoing programming, or when a particular infusion pump 202 is already used in an ongoing infusion, or that the infusion pump 202 is currently executing a bolus or secondary infusion. In some implementations, when a security certificate associated with the communication module 206, for communications and message security, has expired, the unique identifier associated with the infusion pump 202 or the infusion device 204 is either not presented, or is removed. Instead, an error message is provided, either on display 222 of the infusion device 204, or at the workstation to indicate that the security certificate needs to be updated.

Because the infusion device may only be programmed remotely when connected to the system 208, scanning the unique identifier 220 to initiate programming of the infusion pump when the infusion device is not connected to the network wastes valuable time. In this regard, the infusion device may be programmed to provide an alert that it is not connected, and thus cannot be programmed. According to various implementations, by not displaying the unique identifier 220 when no data connection is established between the infusion device 204 and the data network system 208, the caregiver can be more quickly alerted about the lack of data connection. The infusion process may be initiated only after the infusion order is associated to the patient, the bag of medication, and the infusion pump 202. As a result, a success rate of automatically configuring the infusion device to infuse the medical fluid to the patient may increase.

In some implementations, faster visual feedback is provided by the absence of the unique identifier 220 on a display 222 of the infusion device 204 to troubleshoot the lack of data connectivity. APR messages from the EMR may be delivered to the infusion device 204 only after the unique identifier of the infusion device is scanned. Thus, the absence of the unique identifier 220 provides an alert that the unique identifier of the infusion device will not be presented on the display of the infusion device for scanning by the scanner. In some implementations, in addition to not displaying the unique identifier 220 on the display 222, an error message is shown on the display 222, instructing the caregiver to re-establish the data connection between the infusion device 204 and the data network system. In some implementation, in addition to not displaying the unique identifier 220 on the display 222, an error message is additionally shown on the caregiver's workstation. The error message may be provided in the software program on the workstation that is associated with the EMR system 210.

By not displaying the unique identifier 220 on the display 222, the system 200 reduces (e.g., avoids) a chance that the caregiver would be misled into waiting for an infusion order to be sent to the infusion pump 202 when in fact no data connection between the infusion pump 202 and the data network system 208 has been established. In experimental implementations, around 5% of the automatic programming requests (APRs) sent from the EMR system 210 may fail because the infusion pump 202 is not communicating with the data network system 208. Using the system 200, the failure to recognize a lack of data connection between the EMR system 210 and the infusion pump 202 may be reduced to almost zero because the association of the infusion pump 202 cannot be completed without the unique identifier 220 being scanned by the scanner.

When the patient is successfully associated to the medication bag for infusion and the unique identifier associated with a particular infusion pump 202 of the infusion device, the infusion device enables a portion of the user interface on the infusion device 204 to be triggered to request the EMR system 210 to send the infusion order to the infusion pump 202.

The EMR system 210 receives that command from the infusion device 204 and uses the unique identifier 220 (e.g., serial number of the infusion pump 202) scanned by the scanner and medication information entered by the pharmacist to create the auto programming request (APR) message. The APR message is sent to the coordination engine 212. Messages received by the coordination engine 212 may be stored in a tracing database. When the coordination engine determines that the order information is complete and that a system time associated with the EMR system 210 is synchronized with a system time associated with the coordination engine 212 (e.g., within ±15 seconds), the APR message is accepted and an acknowledgement message may be sent back to the EMR system 210. In some implementations, an Infusion Administration Verification screen on the workstation displays a first confirmation at this stage in the process of the APR message. If there are incomplete fields or invalid data (e.g., wrong number of digits in the serial number field) or the system times are not synchronized, an error message may be sent to the EMR system 210, and an error message may be provided.

The information received by the coordination engine is further relayed to the infusion system server 216. The infusion system server 216 is able to query the infusion device serial number for a specific infusion pump 202. In some implementations, the infusion system server 216 is also able to check if the infusion device 204 has a data connection to the infusion system server 216. If the infusion device 204 is offline in the infusion system server 216, an error message (e.g., a negative acknowledgement message) is generated to notify the caregiver that the infusion system server 216 is unable to reach the infusion device 204.

When the infusion device 204 has an active communication to the infusion system server 216, the infusion order information is sent from the infusion system server 216 to the infusion device 204. In some implementations, the infusion device 204 interprets the data associated with the infusion order as a series of manual button presses. Once the infusion order is received, the infusion device 204 checks that the medication contained in the infusion order exists in the online drug library 214 and that the dosing parameters are correct/valid.

After verification of the infusion order details delivered by the APR messages from the EMR system 210 to the infusion device 204, the infusion device enables a start button to be triggered to begin the infusion.

In some implementations, the unique identifier 220 associated with a particular infusion pump 202 is displayed when the infusion pump is ready to receive auto programming requests, and that the following conditions are met: (1) active data connection between the infusion device 204 and the infusion system server 216; (2) active data connection to the coordination engine 212, having the infusion adaptor 218 add-on installed; and (3) active data connection to the online drug library 214 and the drug library is deployed to the infusion system server 216.

In addition, the unique identifier 220 is not displayed unless the infusion device 204 and the infusion pump 202 that receive the infusion order is powered on, is operational (not malfunctioning or displaying an alarm), not currently undergoing programming, not currently executing a bolus or secondary infusion step, the infusion pump 202 to carry out the infusion is not busy with another task, and that the drug library and care area are active on the infusion device 204 and for the infusion pump 202. In some implementations, the infusion device 204 may be in sleep mode. In some implementations, the unique identifier 220 is displayed while in sleep mode to allow the system to wake up when receiving an APR.

Table 1 tabulates eight different examples of auto programming readiness criteria. The criteria may be classified as connection type, configuration type or usage type criteria. Connection type criteria include the presence of an active connection to an infusion pump fleet management server (IFMS), the presence of an active connection to EMR or other health information server (HIS), and the presence of a security certificate (e.g., for communications and message security) on the system that has not expired. Configuration type criteria include whether the IFMS is properly configured, for example, whether an appropriate drug library is connected, and whether the drug library and the care area are active on the PCU and for the module. Usage type criteria include whether the PCU and module are operational, and not malfunctioning or alarming, and whether the module is currently busy with another task. The source of information regarding whether auto programming readiness criteria are met can be from the system manager (SM) or from the PCU or module. The criteria may also be either dynamic or stable. A criterion having a stable characteristic may not change during the initiation of the infusion process or during the infusion process. A criterion having a dynamic characteristic may be more susceptible to changes during the initiation of the infusion process or during the infusion process, and may need to be monitored more frequently.

TABLE 1

| Criteria | Type | Characteristics | Source of information |
| --- | --- | --- | --- |
| 1. Active connection to an infusion pump fleet management server (IFMS) | Connection | dynamic | SM |
| 2. Active connection to EMR or other HIS | Connection | stable | SM |
| 3. IFMS properly configured (e.g., drug library) | Configuration | stable | SM |
| 4. The drug library and care area are active on the PCU and for the module | Configuration | stable | PCU |
| 5. The PCU and module are operational (not malfunction or alarming) | Usage | dynamic | PCU/Module |
| 6. The module is currently not busy with another task: i. not currently undergoing programming; ii. not currently executing a bolus or secondary infusion step. (APR not accepted while module is executing these infusion steps) | Usage | dynamic | PCU/Module |
| 7. The security certificate (e.g., for comms and message security) on the system has not expired. | Connection | dynamic | SM |

In some implementations, each infusion pump 202 controlled by the infusion device 204 has its own independent communication module 206 to communicate with other components in the system 200. The infusion pump 202 may control its own communication module 206, or may receive from control signals from the infusion device 204. In some implementations, the communication module 206 is centrally controlled by the infusion device 204 to coordinate incoming and outgoing communications to and from one or more infusion pumps 202.

In some implementations, the system 200 further includes an infusion module (e.g., a data network system 208, a coordination engine 212, an infusion system server 216, and an online drug library 214) in data communication with the infusion device 204. A processor of the system 200 is configured to determine whether the infusion module is in a prepared state such that the unique identifier is presented based on whether the infusion module is in the prepared state. For example, the unique identifier may be presented if the infusion module is in the prepared state. In some implementations, the infusion device 204 is a volumetric infusion pump or a syringe infusion pump.

FIG. 2B depicts the system shown in FIG. 2A, when the infusion device is not ready for auto programming because there is no data connection between the infusion device and the data network system, according to aspects of the subject technology. When the infusion device 204 does not have a data connection to any of the EMR system 210, the coordination engine 212, the online drug library 214, or the infusion system server 216 in the data network system 208, or that the infusion adaptor 218 has not been installed in the coordination engine 212, no unique identifier 220 (see, e.g., FIG. 2A) would be shown on the display 222 of the infusion device. Without the unique identifier 220, the initiation process of associating the infusion order, the patient, the bag of medication for infusion, and the infusion pump is interrupted. In some implementations, the infusion device 204 may identify the readiness criteria or criterion that were not met and automatically adjust the infusion device 204 to become ready. For example, if the network connection is not established, the infusion device 204 may attempt to retry establishing the connection or attempt to establish a connection via an alternate access point or using alternate connection parameters (e.g., request timeout, transport protocol, credential, network adapter, etc.). In some implementations, adjusting the infusion device 204 may include presenting a prompt or other corrective alert for correcting the detected error, such as a data connectivity or power supply issue.

Figure 3:
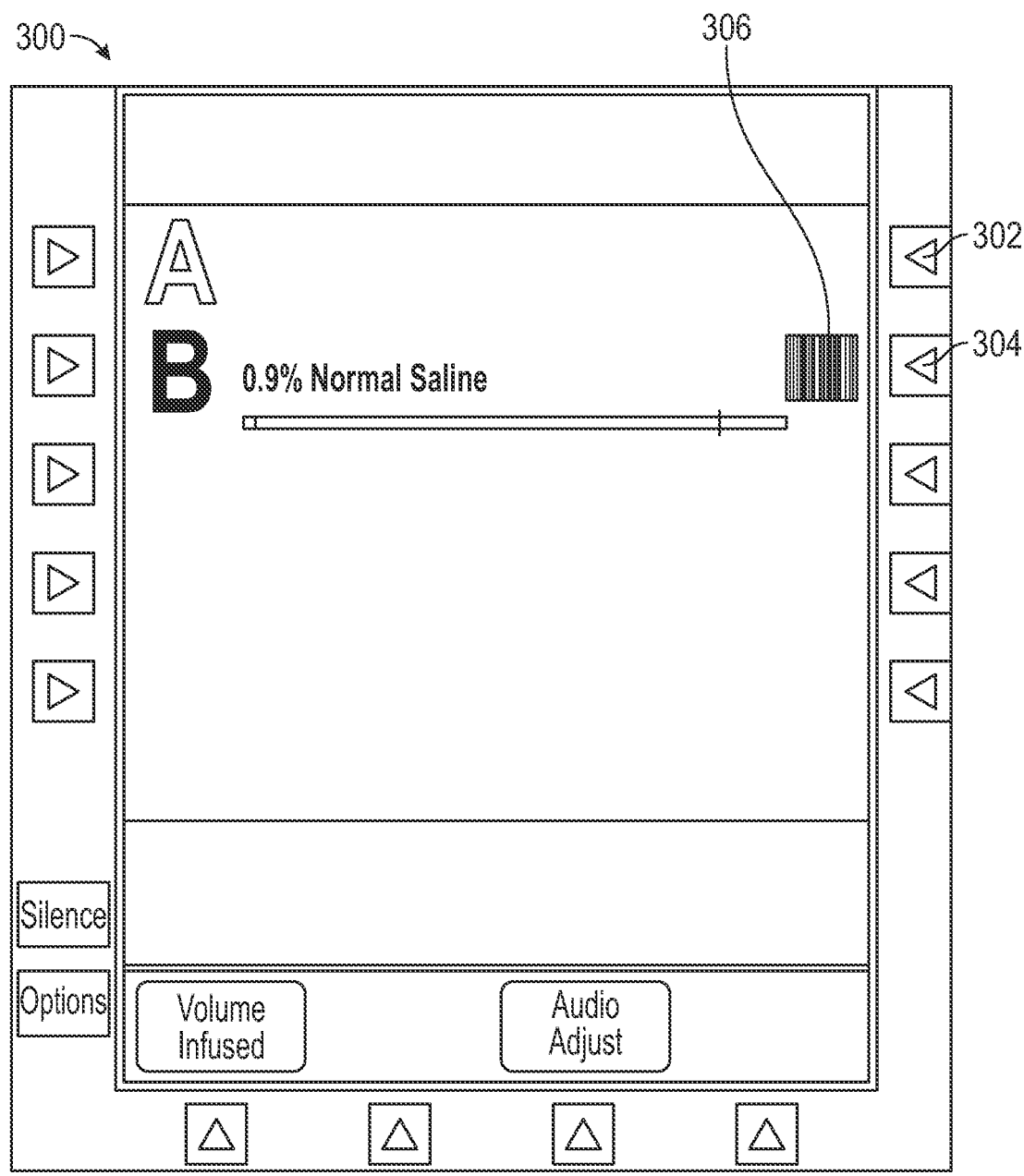
FIG. 3 depicts an example user interface of a system for ensuring the infusion device is in a prepared state to perform the steps needed to program the infusion and execute a programmed infusion, according to aspects of the subject technology.

FIG. 3 depicts an example user interface of a system for ensuring a data connection between an infusion device and a data network system, according to aspects of the subject technology. A user interface 300 is suitable for use in infusion devices that do not have an LCD display. A barcode icon 306 is shown on the infusion device 204 main display next to an identifier of an infusion pump 202.

In some implementations, when an auto programming request (APR) from the EMR system 210 is to be sent to the infusion pump 202 corresponding to the pump channel B, the user interface 300 on the infusion device main page displays a barcode icon 306 next to pump channel B. A softkey 304 next to the barcode icon for channel B may be selected to initiate the APR. A softkey 302 corresponds to an infusion pump corresponding to the pump channel A. The infusion device 204 displays the barcode label for channel B after the softkey 304 is selected. The unique identifier (e.g., barcode) for the infusion pump at channel B may then be scanned.

Figure 4A:
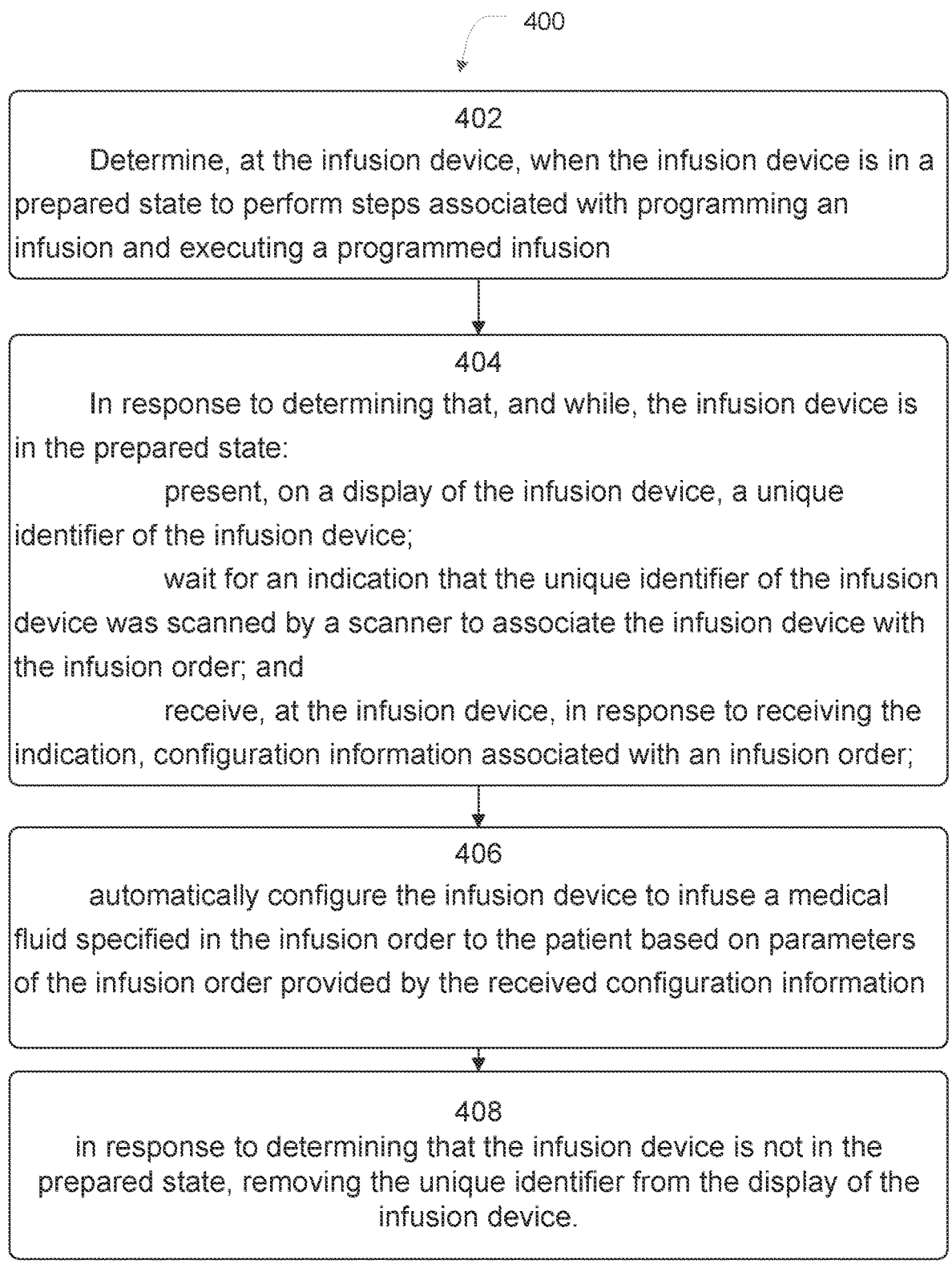
FIG. 4A depicts an example method for ensuring an infusion device is in a prepared state to perform the steps needed to program the infusion and execute a programmed infusion, according to aspects of the subject technology.

FIG. 4A depicts an example method for ensuring an infusion device is in a prepared state to perform the steps needed to program the infusion and execute a programmed infusion, according to aspects of the subject technology. For explanatory purposes, the various blocks of example method 400 are described herein with reference to FIG. 4A, and the components and/or processes described herein. The one or more of the blocks of method 400 may be implemented, for example, by one or more computing devices such as those described above. In some implementations, one or more of the blocks may be implemented apart from other blocks, and by one or more different processors or devices. Further for explanatory purposes, the blocks of example method 400 are described as occurring in serial, or linearly. However, multiple blocks of example method 400 may occur in parallel. In addition, the blocks of example method 400 need not be performed in the order shown and/or one or more of the blocks of example method 400 need not be performed.

In the depicted example, an infusion device determines, when the infusion device is in a prepared state to perform steps associated with programming an infusion and executing a programmed infusion (402). In response to determining that, and while the infusion device is in the prepared state: a unique identifier of the infusion device is presented on a display of the infusion device; wait for an indication that the unique identifier of the infusion device was scanned by a scanner to associate the infusion device with the infusion order; and receive, at the infusion device, in response to receiving the indication, configuration information associated with the infusion order (404). The infusion device is automatically configured to cause infusion of a medical fluid specified in the infusion order based on parameters of the infusion order provided by the received configuration information (406). In response to determining that the infusion device is not in the prepared state, removing the unique identifier from the display of the infusion device. (408).

In some implementations, an infusion system includes an infusion device; a network data transceiver; and a processor configured to: determine, at the infusion device, when the infusion device is in a prepared state; in response to determining that, and while, the infusion device is in the prepared state: present, on a display of the infusion device, a unique identifier of the infusion device; waiting for an indication that the unique identifier of the infusion device was scanned by a scanner to associate the infusion device with an infusion order; and receiving, at the infusion device, in response to receiving the indication, configuration information associated with the infusion order; and automatically configuring the infusion device to cause infusion of a medical fluid specified in the infusion order based on parameters of the infusion order provided by the received configuration information; and in response to determining that the infusion device is not in the prepared state, removing the unique identifier from the display of the infusion device.

In some implementations, the processor is further configured to adjust a network parameter of the infusion device, the network parameter includes at least one of a request timeout, a transport protocol, a credential, or a network adapter, in response to determining that the infusion device is not in the prepared state. The processor is further configured to replace the unique identifier with a perceivable indicator associated with a connection error in response to determining that the infusion device is not in the prepared state. The prepared state includes an active connection to an infusion pump fleet management server, the infusion device is in an operational state, and a security certificate associated with the infusion device that is not expired.

In some implementations, a method of ensuring an infusion device is in a prepared state to perform the steps needed to program an infusion and execute a programmed infusion, the method includes determining, at the infusion device, when the infusion device is in the prepared state. In response to determining that, and while, the infusion device is in the prepared: the method includes presenting, on a display of the infusion device, a unique identifier of the infusion device; waiting for an indication that the unique identifier of the infusion device was scanned by a scanner to associate the infusion device with the infusion order; and receiving, at the infusion device, in response to receiving the indication, configuration information associated with the infusion order. The method includes automatically configuring the infusion device to cause infusion of a medical fluid specified in the infusion order based on parameters of the infusion order provided by the received configuration information. In response to determining that the infusion device is not in the prepared state, removing the unique identifier from the display of the infusion device.

In some implementations, the method further includes determining that the infusion device is in the prepared state further includes determining that the infusion device is in data communication with a coordination engine, an infusion system server, and an online drug library.

In some implementations, the method further includes: in response to determining that the infusion device lacks a data connection between the infusion device and the data network system, displaying, at a user interface of the infusion device, a prompt for an input to cause the infusion device to establish a data connection to the data network system.

In some implementations, determining that, the infusion device is in communication with the electronic medical records storage and retrieval system further includes determining an operational status of the infusion device and wherein the operational status of the infusion device indicates an availability of the infusion device to perform the infusion order.

In some implementations, the unique identifier is presented when the operational status indicates that the infusion device is operational, and the infusion device is not undergoing programming or executing a bolus or secondary infusion. In some implementations, the unique identifier of the infusion device comprises a two-dimensional barcode that is displayed on a display (e.g., liquid crystal display (LCD)) of the infusion device.

In some implementations, the infusion device includes a plurality of infusion pumps, and the unique identifier of the infusion device is associated with a selected one of the plurality of infusion pumps that is available to receive the infusion order.

In some implementations, prior to presenting the unique identifier of the infusion device associated with the selected one of the plurality of infusion pumps on the display of the infusion device, displaying a barcode code icon next to a softkey adjacent the selected one of the plurality of infusion pumps; receiving a selection of the softkey; and in response to receiving the selection of the softkey, initiating an auto programming request.

In some implementations, the electronic medical records storage and retrieval system receives the infusion order from a care provider and transmits an auto programming request to a coordination engine in the data network system upon receiving information contained in the unique identifier of the infusion device.

In some implementations, the infusion device is communicatively connected to the electronic medical records storage and retrieval system via a server system of a care facility that houses the infusion device.

In some implementations, the electronic medical records storage and retrieval system is communicatively coupled to a care facility internal network, the coordination engine, a drug library deployed to the care facility internal network and an infusion system server.

In some implementations, in accordance with a determination that a security certificate associated with a data connection between an infusion system server in the data network system and a coordination engine in the data network system is invalid, generating an alert indicating that the unique identifier of the infusion device will not be presented on the display of the infusion device for scanning by the scanner.

In some implementations, the method further includes adjusting a network parameter of the infusion device, the network parameter comprises at least one of a request timeout, a transport protocol, a credential, or a network adapter, in response to determining that the infusion device is not in the prepared state.

In some implementations, the method further includes replacing the unique identifier with a perceivable indicator associated with a connection error in response to determining that the infusion device is not in the prepared state.

In some implementations, the prepared state includes an active connection to an infusion pump fleet management server, the infusion device is in an operational state, and a security certificate associated with the infusion device that is not expired. In some implementations, the prepared state may include the state (e.g., attached, powered, data connectivity, sensing active, error detected, alarm condition identified, etc.) of a sensor or other accessory providing functionality to or for the infusion device (e.g., barcode scanner, air-in-line sensor, patient monitoring device, etc.).

Figure 4B:
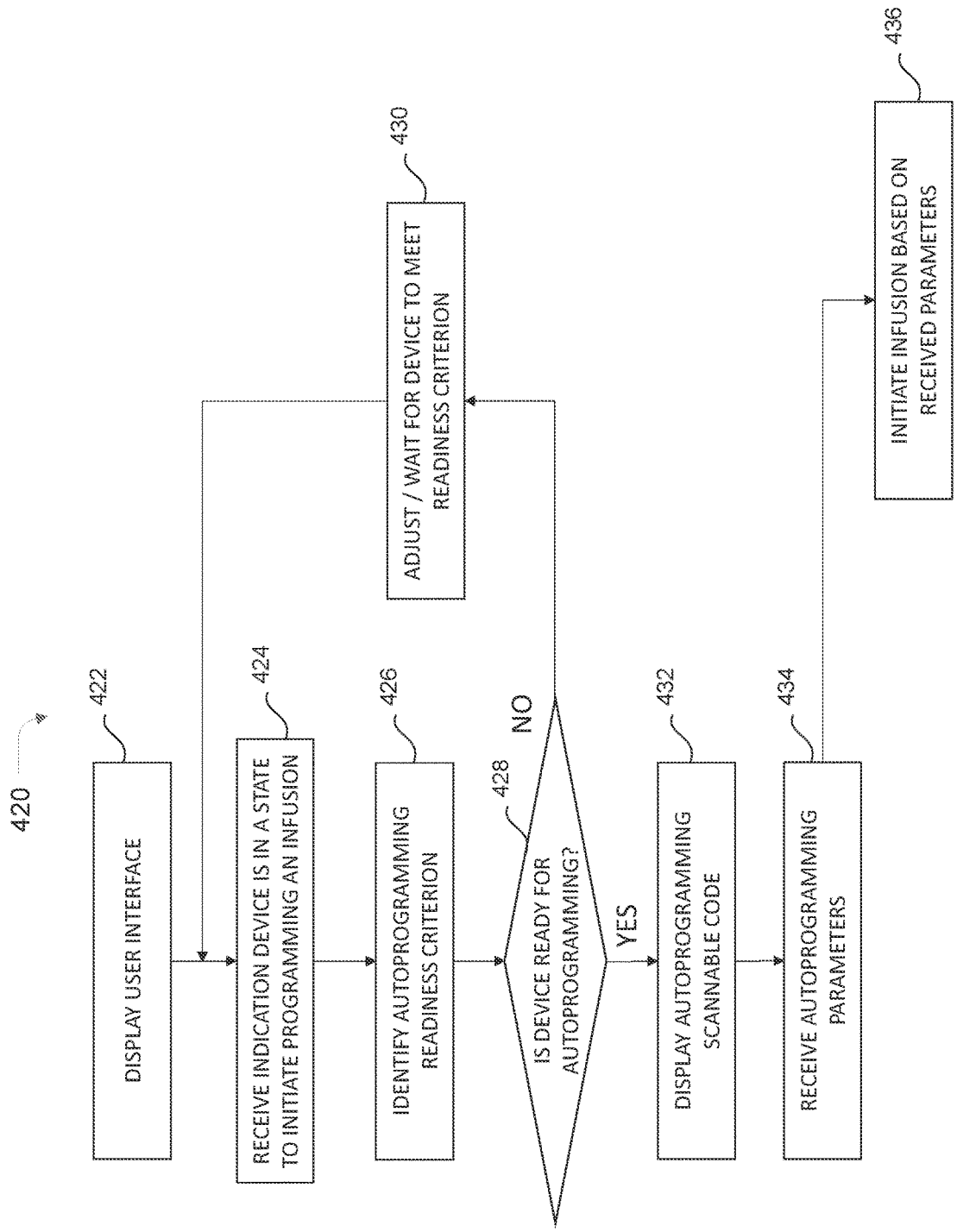
FIG. 4B depicts an example workflow of ensuring an infusion device is in a prepared state to perform the steps needed to program the infusion and execute a programmed infusion, according to aspects of the subject technology.

FIG. 4B depicts an example workflow of ensuring the infusion device is in a prepared state to perform the steps needed to program the infusion and execute a programmed infusion, according to aspects of the subject technology. An example workflow 420 includes displaying, at the infusion device, a user interface (422). Next, the processor in the infusion device receives an indication whether the infusion device is in a prepared state to initiate programming of an infusion (424). The processor identifies an auto programming readiness criterion, for example, as described in Table 1 (426), and determines if the infusion device is ready for auto programming (428). In accordance with a determination that the device is not ready, the infusion device adjusts or waits for the device to meet the readiness criterion (430). In accordance with a determination that the device is ready, the infusion device displays an auto programming scannable code (432), and receives auto programming parameters (434). The infusion device then initiates infusion based on the received parameters (436).

Figure 5:
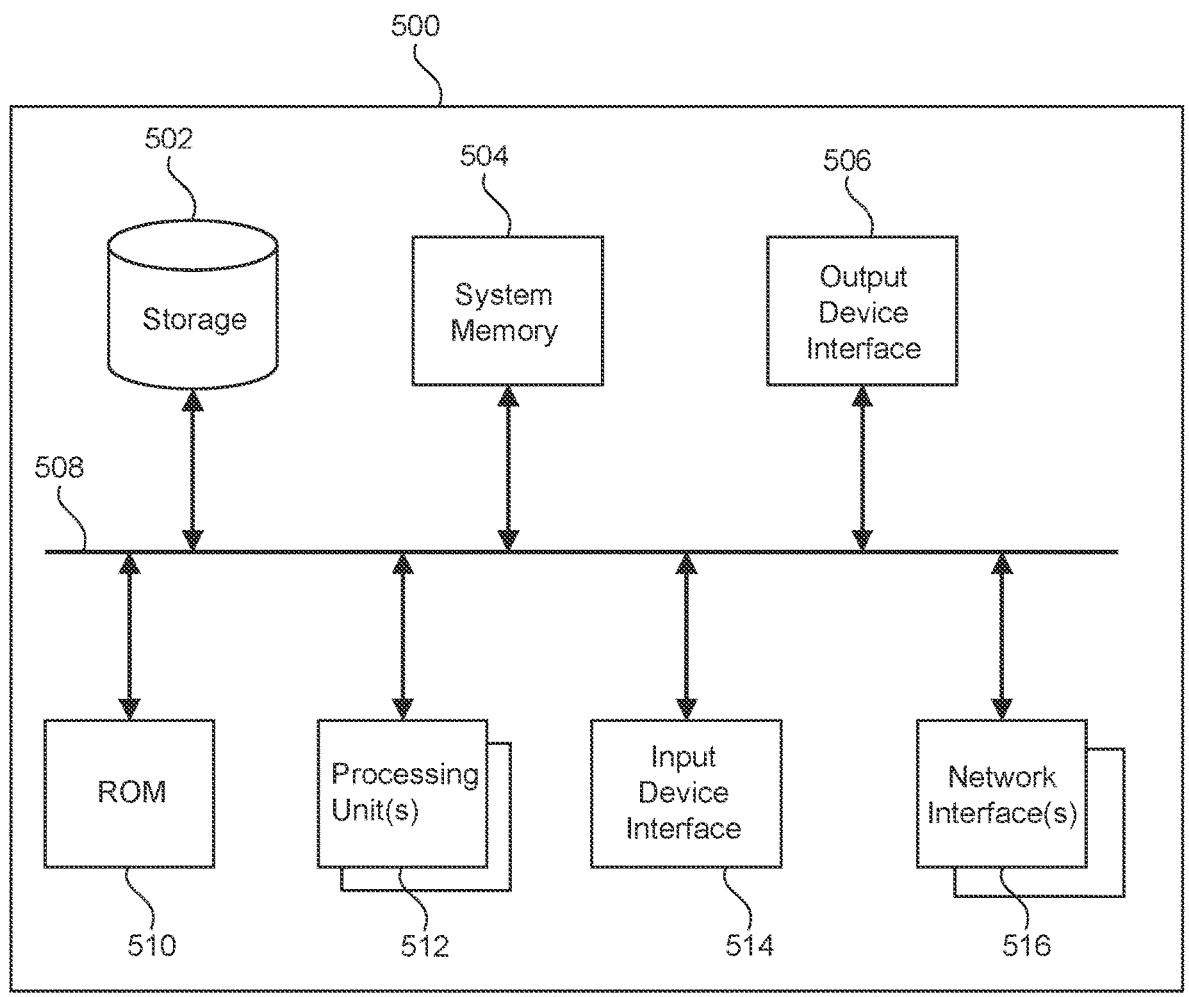
FIG. 5 is a conceptual diagram illustrating an example electronic system for ensuring the infusion device is in a prepared state to perform the steps needed to program the infusion and execute a programmed infusion, according to aspects of the subject technology.

FIG. 5 is a conceptual diagram illustrating an example electronic system for determining a fault condition during an infusion process, according to aspects of the subject technology. Electronic system 500 may be a computing device for execution of software associated with one or more portions or steps of process, or components and processes provided by FIGS. 1-4B, including but not limited to server 130, computing hardware within patient care device 12, terminal device 132, or infusion device 204. Electronic system 500 may be representative, in combination with the disclosure regarding FIGS. 1-4B. In this regard, electronic system 500 may be a personal computer or a mobile device such as a smartphone, tablet computer, laptop, PDA, an augmented reality device, a wearable such as a watch or band or glasses, or combination thereof, or other touch screen or television with one or more processors embedded therein or coupled thereto, or any other sort of computer-related electronic device having network connectivity.

Electronic system 500 may include various types of computer readable media and interfaces for various other types of computer readable media. In the depicted example, electronic system 500 includes a bus 508, processing unit(s) 512, a system memory 504, a read-only memory (ROM) 510, a permanent storage device 502, an input device interface 514, an output device interface 506, and one or more network interfaces 516. In some implementations, electronic system 500 may include or be integrated with other computing devices or circuitry for operation of the various components and processes previously described.

Bus 508 collectively represents all system, peripheral, and chipset buses that communicatively connect the numerous internal devices of electronic system 500. For instance, bus 508 communicatively connects processing unit(s) 512 with ROM 510, system memory 504, and permanent storage device 502.

From these various memory units, processing unit(s) 512 retrieves instructions to execute and data to process in order to execute the processes of the subject disclosure. The processing unit(s) can be a single processor or a multi-core processor in different implementations.

ROM 510 stores static data and instructions that are needed by processing unit(s) 512 and other modules of the electronic system. Permanent storage device 502, on the other hand, is a read-and-write memory device. This device is a non-volatile memory unit that stores instructions and data even when electronic system 500 is off. Some implementations of the subject disclosure use a mass-storage device (such as a magnetic or optical disk and its corresponding disk drive) as permanent storage device 502.

Other implementations use a removable storage device (such as a floppy disk, flash drive, and its corresponding disk drive) as permanent storage device 502. Like permanent storage device 502, system memory 504 is a read-and-write memory device. However, unlike storage device 502, system memory 504 is a volatile read-and-write memory, such a random access memory. System memory 504 stores some of the instructions and data that the processor needs at runtime. In some implementations, the processes of the subject disclosure are stored in system memory 504, permanent storage device 502, and/or ROM 510. From these various memory units, processing unit(s) 512 retrieves instructions to execute and data to process in order to execute the processes of some implementations.

Bus 508 also connects to input and output device interfaces 514 and 506. Input device interface 514 enables the user to communicate information and select commands to the electronic system. Input devices used with input device interface 514 include, e.g., alphanumeric keyboards and pointing devices (also called "cursor control devices"). Output device interfaces 506 enables, e.g., the display of images generated by the electronic system 500. Output devices used with output device interface 506 include, e.g., printers and display devices, such as cathode ray tubes (CRT) or liquid crystal displays (LCD). Some implementations include devices such as a touchscreen that functions as both input and output devices.

Also, as shown in FIG. 5, bus 508 also couples electronic system 500 to a network (not shown) through network interfaces 516. Network interfaces 516 may include, e.g., a wireless access point (e.g., Bluetooth or WiFi) or radio circuitry (e.g., transceiver, antenna, amplifier) for connecting to a wireless access point. Network interfaces 516 may also include hardware (e.g., Ethernet hardware) for connecting the computer to a part of a network of computers such as a local area network ("LAN"), a wide area network ("WAN"), wireless LAN, personal area network ("PAN"), or an Intranet, or a network of networks, such as the Internet. Any or all components of electronic system 500 can be used in conjunction with the subject disclosure.

These functions described above can be implemented in computer software, firmware or hardware. The techniques can be implemented using one or more computer program products. Programmable processors and computers can be included in or packaged as mobile devices. The processes and logic flows can be performed by one or more programmable processors and by one or more programmable logic circuitry. General and special purpose computing devices and storage devices specifically configured for the infusion features described can be interconnected through communication networks.

Some implementations include electronic components, such as microprocessors, storage and memory that store computer program instructions in a machine-readable or computer-readable medium (also referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, read-only and recordable Blu-Ray® discs, ultra density optical discs, any other optical or magnetic media, and floppy disks. The computer-readable media can store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter.

While the above discussion primarily refers to microprocessor or multi-core processors that execute software, some implementations are performed by one or more integrated circuits, such as application specific integrated circuits (ASICs) or field programmable gate arrays (FPGAs). In some implementations, such integrated circuits execute instructions that are stored on the circuit itself.

As used in this specification and any claims of this application, the terms "computer", "server", "processor", and "memory" all refer to electronic or other technological devices. These terms exclude people or groups of people. For the purposes of the specification, the terms display or displaying means displaying on an electronic device. As used in this specification and any claims of this application, the terms "computer readable medium" and "computer readable media" are entirely restricted to tangible, physical objects that store information in a form that is readable by a computer. These terms exclude any wireless signals, wired download signals, and any other ephemeral signals.

To provide for interaction with a user, implementations of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; e.g., feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; e.g., by sending web pages to a web browser on a user's client device in response to requests received from the web browser.

Embodiments of the subject matter described in this specification can be implemented in a specifically configured computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

The computing system can include clients and servers. A client and server are generally remote from each other and may interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

Those of skill in the art would appreciate that the various illustrative blocks, modules, elements, components, methods, and algorithms described herein may be implemented as electronic hardware, computer software, or combinations of both. To illustrate this interchangeability of hardware and software, various illustrative blocks, modules, elements, components, methods, and algorithms have been described above generally in terms of their functionality. Whether such functionality is implemented as hardware or software depends upon the particular application and design constraints imposed on the overall system. The described functionality may be implemented in varying ways for each particular application. Various components and blocks may be arranged differently (e.g., arranged in a different order, or partitioned in a different way) all without departing from the scope of the subject technology.

It is understood that the specific order or hierarchy of steps in the processes disclosed is an illustration of example approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Illustration of Subject Technology as Clauses

Various examples of aspects of the disclosure are described as numbered clauses (1, 2, 3, etc.) for convenience. These are provided as examples, and do not limit the subject technology. Identifications of the figures and reference numbers are provided below merely as examples and for illustrative purposes, and the clauses are not limited by those identifications.

Clause 1. An infusion system comprising: an infusion device; a network data transceiver; and a processor configured to: determine, at the infusion device, when the infusion device is in a prepared state; in response to determining that, and while, the infusion device is in the prepared state: present, on a display of the infusion device, a unique identifier of the infusion device; wait for an indication that the unique identifier of the infusion device was scanned by a scanner to associate the infusion device with an infusion order; receive, at the infusion device, in response to receiving the indication, configuration information associated with the infusion order; and automatically configure the infusion device to cause infusion of a medical fluid specified in the infusion order based on parameters of the infusion order provided by the received configuration information; and in response to determining that the infusion device is not in the prepared state, removing the unique identifier from the display of the infusion device.

Clause 2. The infusion system of Clause 1, wherein the processor is further configured to adjust a network parameter of the infusion device, the network parameter comprises at least one of a request timeout, a transport protocol, a credential, or a network adapter, in response to determining that the infusion device is not in the prepared state.

Clause 3. The infusion system of Clause 1 or Clause 2, wherein the processor is further configured to replace the unique identifier with a perceivable indicator associated with a connection error in response to determining that the infusion device is not in the prepared state.

Clause 4. The infusion system of any of Clauses 1-3, wherein the prepared state includes an active connection to an infusion pump fleet management server, the infusion device is in an operational state, and a security certificate associated with the infusion device that is not expired.

Clause 5. The infusion system of any of Clauses 1-4, further comprising an infusion module in data communication with the infusion device, and wherein the processor is further configured to determine whether the infusion module is in a prepared state, wherein the unique identifier is presented if the infusion module is in the prepared state.

Clause 6. The infusion system of any of Clauses 1-5, wherein the infusion device comprises one of: a volumetric infusion pump or a syringe infusion pump.

Clause 7. A method of ensuring an infusion device is in a prepared state to perform steps associated with programming an infusion and executing a programmed infusion, the method comprising: determining, at the infusion device, when the infusion device is in the prepared state; in response to determining that, and while, the infusion device is in a prepared state: presenting, on a display of the infusion device, a unique identifier of the infusion device; waiting for an indication that the unique identifier of the infusion device was scanned by a scanner to associate the infusion device with the infusion order; receiving, at the infusion device, in response to receiving the indication, configuration information associated with an infusion order; and automatically configuring the infusion device to cause infusion of a medical fluid specified in the infusion order based on parameters of the infusion order provided by the received configuration information; and in response to determining that the infusion device is not in a prepared state, removing the unique identifier from the display of the infusion device.

Clause 8. The method of Clause 7, wherein determining that the infusion device is in the prepared state further comprises determining that the infusion device is in data communication with a coordination engine, an infusion system server, and an online drug library.

Clause 9. The method of Clauses 7 or 8, wherein the method further includes: in response to determining that the infusion device lacks a data connection between the infusion device and the data network system, displaying, at a user interface of the infusion device, a prompt for an input to cause the infusion device to establish a data connection to the data network system.

Clause 10. The method of any of Clauses 7-9, further comprising: determining an operational status of the infusion device and wherein the operational status of the infusion device indicates an availability of the infusion device to perform the infusion order.

Clause 11. The method of Clause 10, wherein the unique identifier is presented when an operational status indicates that the infusion device is operational, and the infusion device is not undergoing programming or executing a bolus or secondary infusion.

Clause 12. The method of any of Clauses 7-11, wherein the unique identifier of the infusion device comprises a two-dimensional barcode that is displayed on a liquid crystal display (LCD) of the infusion device.

Clause 13. The method of any of Clauses 7-12, wherein the infusion device comprises a plurality of infusion pumps, and the unique identifier of the infusion device is associated with a selected one of the plurality of infusion pumps that is available to receive the infusion order.

Clause 14. The method of Clause 13, wherein: prior to presenting the unique identifier of the infusion device associated with the selected one of the plurality of infusion pumps on the display of the infusion device, displaying a barcode code icon next to a softkey adjacent the selected one of the plurality of infusion pumps; receiving a selection of the softkey; and in response to receiving the selection of the softkey, initiating an auto programming request.

Clause 15. The method of any of Clauses 7-14, wherein the electronic medical records storage and retrieval system receives the infusion order and transmits an auto programming request to a coordination engine in the data network system upon receiving information contained in the unique identifier of the infusion device.

Clause 16. The method of Clause 15, wherein the coordination engine, a drug library deployed to a care facility internal network and an infusion system server are in data communication.

Clause 17. The method of any of Clauses 7-16, further comprising: in accordance with a determination that a security certificate associated with a data connection between an infusion system server in the data network system and a coordination engine in the data network system is invalid, generating an alert indicating that the unique identifier of the infusion device will not be presented on the display of the infusion device for scanning by the scanner.

Clause 18. The method of any of Clauses 7-17, further comprising adjusting a network parameter of the infusion device, the network parameter comprises at least one of a request timeout, a transport protocol, a credential, or a network adapter, in response to determining that the infusion device is not in the prepared state.

Clause 19. The method of any of Clauses 7-18, further comprising replacing the unique identifier with a perceivable indicator associated with a connection error in response to determining that the infusion device is not in the prepared state.

Clause 20. The method of any of Clauses 7-19, wherein the prepared state includes an active connection to an infusion pump fleet management server, the infusion device is in an operational state, and a security certificate associated with the infusion device that is not expired.

Further Consideration

It is understood that the specific order or hierarchy of steps in the processes disclosed is an illustration of example approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

The previous description is provided to enable any person skilled in the art to practice the various aspects described herein. The previous description provides various examples of the subject technology, and the subject technology is not limited to these examples. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention described herein.

The term website, as used herein, may include any aspect of a website, including one or more web pages, one or more servers used to host or store web related content, etc. Accordingly, the term website may be used interchangeably with the terms web page and server. The predicate words "configured to", "operable to", and "programmed to" do not imply any particular tangible or intangible modification of a subject, but, rather, are intended to be used interchangeably. For example, a processor configured to monitor and control an operation or a component may also mean the processor being programmed to monitor and control the operation or the processor being operable to monitor and control the operation. Likewise, a processor configured to execute code can be construed as a processor programmed to execute code or operable to execute code.

The term automatic, as used herein, may include performance by a computer or machine without user intervention; for example, by instructions responsive to a predicate action by the computer or machine or other initiation mechanism. The word "example" is used herein to mean "serving as an example or illustration." Any aspect or design described herein as "example" is not necessarily to be construed as preferred or advantageous over other aspects or designs.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all implementations, or one or more implementations. An embodiment may provide one or more examples. A phrase such as an "embodiment" may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such as a "configuration" may refer to one or more configurations and vice versa.

As used herein, the terms "determine" or "determining" encompass a wide variety of actions. For example, "determining" may include calculating, computing, processing, deriving, generating, obtaining, looking up (e.g., looking up in a table, a database or another data structure), ascertaining and the like via a hardware element without user intervention. Also, "determining" may include receiving (e.g., receiving information), accessing (e.g., accessing data in a memory) and the like via a hardware element without user intervention. "Determining" may include resolving, selecting, choosing, establishing, and the like via a hardware element without user intervention.

As used herein, the terms "provide" or "providing" encompass a wide variety of actions. For example, "providing" may include storing a value in a location of a storage device for subsequent retrieval, transmitting a value directly to the recipient via at least one wired or wireless communication medium, transmitting or storing a reference to a value, and the like. "Providing" may also include encoding, decoding, encrypting, decrypting, validating, verifying, and the like via a hardware element.

As used herein, the term "message" encompasses a wide variety of formats for communicating (e.g., transmitting or receiving) information. A message may include a machine readable aggregation of information such as an XML document, fixed field message, comma separated message, JSON, a custom protocol, or the like. A message may, in some embodiments, include a signal utilized to transmit one or more representations of the information. While recited in the singular, it will be understood that a message may be composed, transmitted, stored, received, etc. in multiple parts.

As used herein, the terms "correspond" or "corresponding" encompasses a structural, functional, quantitative and/or qualitative correlation or relationship between two or more objects, data sets, information and/or the like, preferably where the correspondence or relationship may be used to translate one or more of the two or more objects, data sets, information and/or the like so to appear to be the same or equal. Correspondence may be assessed using one or more of a threshold, a value range, fuzzy logic, pattern matching, a machine learning assessment model, or combinations thereof.

In any embodiment, data generated or detected can be forwarded to a "remote" device or location, where "remote," means a location or device other than the location or device at which the program is executed. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but separated, or at least in different rooms or different buildings, and can be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computer or networked device, and the internet or cellular networks.

What is claimed is:

1. An infusion system comprising:
an infusion device;
a network data transceiver; and
a processor configured to:
determine, at the infusion device, whether the infusion device is in a prepared state to receive an automated programming request;
in response to determining that, and while, the infusion device is in the prepared state:
present, on a display of the infusion device, a unique identifier of the infusion device;
wait for an indication that the unique identifier of the infusion device was scanned by a scanner to associate the infusion device with an infusion order;
receive from a data network system, at the infusion device, in response to receiving the indication, configuration information associated with the infusion order; and
automatically configure the infusion device to cause infusion of a medical fluid specified in the infusion order to a patient based on parameters of the infusion order provided by the received configuration information; and
in response to determining that the infusion device is not in the prepared state:
not presenting the unique identifier from the display of the infusion device;
identifying an error associated with the infusion device not being ready to receive the automated programming request;
automatically adjusting the infusion device to correct the error based on one or more connection type, configuration type, or usage type parameters associated with the infusion device;
adjusting a network parameter of the infusion device, the network parameter comprises a transport protocol or a credential; and
causing the infusion device to administer the medical fluid specified in the infusion order to the patient after the infusion device has been adjusted to correct the error.

2. The infusion system of claim 1, wherein the processor is further configured to replace the unique identifier with a perceivable indicator associated with a connection error in response to determining that the infusion device is not in the prepared state.

3. The infusion system of claim 1, wherein the prepared state includes an active connection to an infusion pump fleet management server, the infusion device is in an operational state, and a security certificate associated with the infusion device that is not expired.

4. The infusion system of claim 1, further comprising an infusion module in data communication with the infusion device, and wherein the processor is further configured to determine whether the infusion module is in a prepared state, wherein the unique identifier is presented if the infusion module is in the prepared state.

5. The infusion system of claim 1, wherein the infusion device comprises one of: a volumetric infusion pump or a syringe infusion pump.

6. A method of ensuring an infusion device is in a prepared state to perform steps associated with programming an infusion and executing a programmed infusion, the method comprising:
  determining, at the infusion device, whether the infusion device is in the prepared state to receive an automated programming request;
  in response to determining that, and while, the infusion device is in a prepared state:
    presenting, on a display of the infusion device, a unique identifier of the infusion device;
    waiting for an indication that the unique identifier of the infusion device was scanned by a scanner to associate the infusion device with the infusion order;
    receiving, at the infusion device, in response to receiving the indication, configuration information associated with an infusion order; and
    automatically configuring the infusion device to cause an infusion of a medical fluid specified in the infusion order to a patient based on parameters of the infusion order provided by the received configuration information; and
  in response to determining that the infusion device is not in a prepared state:
    not presenting the unique identifier from the display of the infusion device;
    identifying an error associated with the infusion device not being ready to receive the automated programming request;
    automatically adjusting the infusion device to correct the error based on one or more connection type, configuration type, or usage type parameters associated with the infusion device;
    adjusting a network parameter of the infusion device, the network parameter comprises a transport protocol or a credential; and
    causing the infusion device to administer the medical fluid specified in the infusion order to the patient after the infusion device has been adjusted to correct the error.

7. The method of claim 6, wherein
  determining that the infusion device is in the prepared state further comprises determining that the infusion device is in data communication with a coordination engine, an infusion system server, and an online drug library.

8. The method of claim 6, wherein the method further includes:
  in response to determining that the infusion device lacks a data connection between the infusion device and the data network system, displaying, at a user interface of the infusion device, a prompt for an input to cause the infusion device to establish a data connection to the data network system.

9. The method of claim 6, further comprising:
  determining an operational status of the infusion device and wherein the operational status of the infusion device indicates an availability of the infusion device to perform the infusion order.

10. The method of claim 9, wherein the unique identifier is presented when an operational status indicates that the infusion device is operational, and the infusion device is not undergoing programming or executing a bolus or secondary infusion.

11. The method of claim 6, wherein the unique identifier of the infusion device comprises a two-dimensional barcode that is displayed on a liquid crystal display (LCD) of the infusion device.

12. The method of claim 6, wherein the infusion device comprises a plurality of infusion pumps, and the unique identifier of the infusion device is associated with a selected one of the plurality of infusion pumps that is available to receive the infusion order.

13. The method of claim 12, wherein:
  prior to presenting the unique identifier of the infusion device associated with the selected one of the plurality of infusion pumps on the display of the infusion device, displaying a barcode code icon next to a softkey adjacent the selected one of the plurality of infusion pumps; receiving a selection of the softkey; and in response to receiving the selection of the softkey, initiating an auto programming request.

14. The method of claim 6, wherein the electronic medical records storage and retrieval system receives the infusion order and transmits an auto programming request to a coordination engine in the data network system upon receiving information contained in the unique identifier of the infusion device.

15. The method of claim 14, wherein the coordination engine, a drug library deployed to a care facility internal network and an infusion system server are in data communication.

16. The method of claim 6, further comprising:
  in accordance with a determination that a security certificate associated with a data connection between an infusion system server in the data network system and a coordination engine in the data network system is invalid, generating an alert indicating that the unique identifier of the infusion device will not be presented on the display of the infusion device for scanning by the scanner.

17. The method of claim 6, further comprising replacing the unique identifier with a perceivable indicator associated with a connection error in response to determining that the infusion device is not in the prepared state.

18. The method of claim 6, wherein the prepared state includes an active connection to an infusion pump fleet management server, the infusion device is in an operational state, and a security certificate associated with the infusion device that is not expired.

* * * * *